(12) United States Patent
McVicker (10) Patent No.: US 7,490,773 B2
(45) Date of Patent: Feb. 17, 2009

(54) APPARATUS AND METHOD FOR OBTAINING AN IMAGE OF AN ARCUATE SURFACE

(76) Inventor: Henry J. McVicker, 4100 Cutlass La., Naples, FL (US) 34102

( * ) Notice: Subject to any disclaimer, the term of this patent is extended or adjusted under 35 U.S.C. 154(b) by 344 days.

(21) Appl. No.: 11/004,071

(22) Filed: Dec. 3, 2004

(65) Prior Publication Data

US 2006/0120751 A1 Jun. 8, 2006

(51) Int. Cl.
G06K 7/00 (2006.01)
G06K 7/10 (2006.01)
G06K 7/14 (2006.01)
G06K 5/00 (2006.01)
G06K 15/12 (2006.01)
G06K 9/20 (2006.01)
G03B 7/08 (2006.01)

(52) U.S. Cl. .......... 235/462.24; 235/435; 235/454; 235/462.24; 235/462.41; 382/321

(58) Field of Classification Search ......... 250/555–557; 382/100, 112, 152, 312, 321, 323; 235/435, 235/454, 462.24, 462.41

See application file for complete search history.

(56) References Cited

U.S. PATENT DOCUMENTS

| | | | | | |
|---|---|---|---|---|---|
| 3,573,472 | A | * | 4/1971 | Madalo | 250/371 |
| 3,955,179 | A | * | 5/1976 | Planke | 382/142 |
| 4,042,960 | A | * | 8/1977 | Wooding, Jr. | 348/331 |
| 4,055,834 | A | * | 10/1977 | Planke | 382/142 |
| 4,244,650 | A | * | 1/1981 | Garfunkel et al. | 356/71 |
| 4,414,566 | A | * | 11/1983 | Peyton et al. | 382/142 |
| 4,563,739 | A | * | 1/1986 | Gerpheide et al. | 705/28 |
| 4,656,510 | A | * | 4/1987 | Mattila | 348/61 |
| 4,664,289 | A | * | 5/1987 | Shimizu et al. | 221/2 |
| 4,885,461 | A | * | 12/1989 | Mattila et al. | 250/223 B |
| 5,028,769 | A | * | 7/1991 | Claypool et al. | 235/454 |
| 5,072,108 | A | * | 12/1991 | Ishikawa | 250/223 B |
| 5,126,556 | A | * | 6/1992 | Domenico et al. | 250/223 B |

(Continued)

OTHER PUBLICATIONS http://www.foss.dk/c/p/solutions/products/showprodfamily.asp-?prodfamilypkid=62; "WineScan™ FT 120"; Oct. 25, 2004; 2 pgs.

(Continued)

Primary Examiner—Daniel Walsh
(74) Attorney, Agent, or Firm—McDonnell Boehnen Hulbert & Berghoff LLP (57) ABSTRACT

A method and apparatus for imaging an arcuate surface of an object such as a bottle with a label thereon. Such bottle may be a wine bottle. In one embodiment, the bottle is placed into an imaging chamber. Preferably, space between the imaging chamber and the wine bottle is covered with a flexible material to exclude light from the chamber. A scanner, or imaging device, is moved either manually or under the control of a microprocessor with respect to the bottle to image the bottle label. Either the scanner travels along an arcuate path around the bottle or the bottle rotates on a turntable to cause the label to move past a stationary scanner. A controller is associated with the imaging device and/or the turntable to control movement of the imaging device or the turntable to cause imaging of the bottle label. The image of the scanned label may be stored in memory, sent to a printer, or wirelessly transmitted to remote storage and/or output devices.

30 Claims, 4 Drawing Sheets

U.S. PATENT DOCUMENTS

| | | | | |
|---|---|---|---|---|
| 5,231,278 A * | 7/1993 | Kuo | | 235/462.49 |
| 5,286,959 A * | 2/1994 | Demachi | | 235/462.14 |
| 5,380,045 A * | 1/1995 | Comann | | 283/70 |
| 5,405,015 A * | 4/1995 | Bhatia et al. | | 209/524 |
| 5,420,408 A * | 5/1995 | Weyrauch et al. | | 235/454 |
| 5,459,819 A * | 10/1995 | Watkins et al. | | 358/1.18 |
| 5,499,718 A * | 3/1996 | Bhatia et al. | | 209/524 |
| 5,535,536 A * | 7/1996 | Comann | | 40/310 |
| 5,603,430 A * | 2/1997 | Loehrke et al. | | 222/1 |
| 5,637,854 A * | 6/1997 | Thomas | | 235/462.14 |
| 5,647,600 A * | 7/1997 | Booras | | 280/47.35 |
| 5,786,582 A * | 7/1998 | Roustaei et al. | | 235/462.07 |
| 5,794,788 A * | 8/1998 | Massen | | 209/524 |
| 5,953,170 A * | 9/1999 | Glancy | | 359/896 |
| 5,986,219 A * | 11/1999 | Carroll et al. | | 177/1 |
| 6,028,302 A * | 2/2000 | Wiejak et al. | | 250/223 B |
| 6,137,900 A * | 10/2000 | Steidel et al. | | 382/142 |
| 6,155,485 A * | 12/2000 | Coughlin et al. | | 235/383 |
| 6,272,777 B1 * | 8/2001 | Swenson | | 40/310 |
| 6,275,603 B1 * | 8/2001 | Cronshaw et al. | | 382/142 |
| 6,360,948 B1 * | 3/2002 | Yang et al. | | 235/462.1 |
| 6,450,406 B2 * | 9/2002 | Brown | | 235/462.45 |
| 6,556,690 B1 * | 4/2003 | Nelson | | 382/100 |
| 6,598,796 B2 * | 7/2003 | Harrop | | 235/462.01 |
| 6,616,037 B2 * | 9/2003 | Grimm et al. | | 235/385 |
| 6,672,510 B2 * | 1/2004 | Sauve | | 235/462.07 |
| 6,726,094 B1 * | 4/2004 | Rantze et al. | | 235/379 |
| 6,746,053 B1 * | 6/2004 | Afzali-Ardakani et al. | | 283/72 |
| 6,817,538 B2 * | 11/2004 | Afzali-Ardakani et al. | | 235/494 |
| 6,989,857 B2 * | 1/2006 | Furnas | | 348/127 |
| 7,028,723 B1 * | 4/2006 | Alouani et al. | | 141/83 |
| 2002/0082027 A1 * | 6/2002 | Nagata | | 455/456 |
| 2002/0097195 A1 * | 7/2002 | Frank | | 345/5 |
| 2002/0114733 A1 * | 8/2002 | Copeland et al. | | 422/64 |
| 2002/0191174 A1 * | 12/2002 | Yamagishi et al. | | 355/133 |
| 2003/0012421 A1 * | 1/2003 | Werzinger | | 382/142 |
| 2003/0034392 A1 * | 2/2003 | Grimm et al. | | 235/385 |
| 2003/0074218 A1 * | 4/2003 | Liff et al. | | 705/1 |
| 2003/0116629 A1 * | 6/2003 | Sauve | | 235/462.07 |
| 2003/0179920 A1 * | 9/2003 | Hooker et al. | | 382/141 |
| 2004/0018289 A1 * | 1/2004 | McQueeny et al. | | 426/538 |
| 2004/0073574 A1 * | 4/2004 | Shimizu et al. | | 707/104.1 |
| 2004/0215486 A1 * | 10/2004 | Braverman | | 705/2 |
| 2005/0103853 A1 * | 5/2005 | Stephenson et al. | | 235/462.15 |
| 2005/0150957 A1 * | 7/2005 | Lubow | | 235/462.01 |
| 2005/0211593 A1 * | 9/2005 | Budin | | 206/459.5 |
| 2005/0252966 A1 * | 11/2005 | Kulas | | 235/383 |
| 2005/0252973 A1 * | 11/2005 | Itoh | | 235/462.01 |
| 2006/0032923 A1 * | 2/2006 | Krupa | | 235/462.01 |
| 2006/0120751 A1 * | 6/2006 | McVicker | | 399/107 |
| 2006/0120752 A1 * | 6/2006 | McVicker et al. | | 399/107 |
| 2006/0131404 A1 * | 6/2006 | Dervishian | | 235/385 |
| 2006/0144938 A1 * | 7/2006 | David | | 235/385 |
| 2006/0208172 A1 * | 9/2006 | Akkerman et al | | 250/223 B |
| 2006/0225593 A1 * | 10/2006 | Flynn et al. | | 101/483 |
| 2006/0225991 A1 * | 10/2006 | Lutz et al. | | 198/607 |
| 2006/0228508 A1 * | 10/2006 | Flynn et al. | | 428/40.1 |
| 2006/0283145 A1 * | 12/2006 | Weisgerber et al. | | 53/167 |
| 2007/0042684 A1 * | 2/2007 | Park | | 451/29 |
| 2007/0143190 A1 * | 6/2007 | Banerjee et al. | | 705/26 |
| 2007/0191983 A1 * | 8/2007 | Griffits et al. | | 700/213 |
| 2007/0262145 A1 * | 11/2007 | LaRue | | 235/454 |
| 2008/0056556 A1 * | 3/2008 | Eller et al. | | 382/142 |
| 2008/0140432 A1 * | 6/2008 | Fenn | | 705/1 |

OTHER PUBLICATIONS http://www.winejotter.com; "Wine Jotter from PocketWorks"; Oct. 25, 2004; 3 pgs.

http://www.uncork.com.au/contact.htm; "The Uncorked Cellar"; Oct. 25, 2004; 1 pg.

http://www.wineryexchange.net/cgi-bin/wineryexchange/infocenter/premiumWineScan.js...; "Winery Exchange"; Oct. 25, 2004; 1 pg.

http://www.vinlab.com/Thewinescan.html; "VinLab your winemaking tool"; Oct. 25, 2004; 1 pg.

http://www.winewares.com/label_lib.html; "Wine Wares.com—Very special wine gifts, accessories, clothing and art;" Oct. 25, 2004; 2 pgs.

http://www.winelabels.org/remove.htm; "Unusual Wines—Removing Labels"; May 24, 2004; 5 pgs.

* cited by examiner

APPARATUS AND METHOD FOR OBTAINING AN IMAGE OF AN ARCUATE SURFACE

BACKGROUND OF THE INVENTION

1. Field of the Invention

The invention relates in general to an apparatus and method for obtaining images with scanning devices, and in particular to a method and apparatus for scanning bottle labels and more specifically to a method and apparatus for scanning wine bottle labels.

2. Description of the Prior Art

The wine industry and its enthusiasts have shown a continuing interest in collecting information from wine bottle labels. Such information is typically used for one or more purposes including recordation of the date, style, and producer as they relate to the quality and value of the wine. Another purpose is for collectors to keep a record of the artistic content of the label along with notes on the consumptive experience.

Numerous methods to remove labels from the wine bottles have been tried including soaking, steaming, adhesive carrier removal, and scraping with a razor. The most popular method employs the use of a clear adhesive tape that is placed over the label and them removed, thereby pulling the label off of the bottle. As can be readily understood, this method often leaves part of the label on the bottle depending on the tenacity of the label's original adhesive. In some varieties of wines, a traditional paper label is substituted with a painted label that is a permanent part of the bottle.

Two less popular methods for collecting label information utilize either photography or placing the bottle on a flatbed scanning device. These methods usually produce poor results because both flatbed scanners and cameras are unable to focus consistently due to the curved surface of the bottle; specifically with respect to photography, there are many variables that would have to be adjusted, and such adjustments would require a person highly skilled in photography to make acceptable images. These techniques therefore are not commonly used.

Barcode labels have become increasingly common on wine bottles. Typically, the barcode label is a supplemental label separate from the manufacturer's primary label. The bar-coded label can be scanned using standard scanning systems for sales and inventory purposes. In some instances, private collectors also use a bar coded system to keep track of their wine cellar inventory. In both commercial and private applications, the scanned information is typically stored and analyzed using a variety of commonly available software programs.

It would be advantageous to have a simple device that is easily operated and that captures a sharp, photographic quality image of the manufacturer's label on a wine bottle such that the image and its related information can be transferred to a variety of output or storage devices.

SUMMARY OF THE INVENTION

In its broadest sense, the present invention relates to a method and apparatus for imaging an arcuate surface, the apparatus comprising a first device for providing a focused image of the arcuate surface that is compensated for depth of field differences; and a second device for receiving and recording the focused image of the arcuate surface. In one embodiment, the present invention is a novel apparatus that uses a scanner to capture a sharp, photographic quality image of the manufacturer's label on a wine bottle. The scanning apparatus is associated with a cylindrical imaging chamber having an open top and a substantially closed bottom. In one embodiment, the imaging chamber may comprise two partial cylinders in order to allow adjustability for different diameter bottles. A wine bottle is placed into the imaging chamber through the opening in the top thereof. Preferably, the space between the bottle and the open top of the imaging chamber is sealed with a flexible skirt to exclude any ambient light. The scanner associated with the imaging chamber travels in at least an arcuate path with respect to the bottle along a given radius from the center of the chamber to scan the image. Alternatively, a rotating base such as a rotatable turntable or series of rollers may be placed in the bottom of the imaging chamber to receive the wine bottle and, upon command from a controller, rotates at a given speed past a fixed scanner associated with the chamber to image the label. Where the rotating base is used, a centering means may be provided to insure the bottle rotates on a centered axis.

In yet another embodiment, the imaging chamber is configured as a curved cradle comprising a series of rollers and a fixed scanning element. A bottle is placed horizontally on the rollers. One or more of the rollers is powered by a motor and drive system used to rotate the bottle whereby the label passes across the fixed scanning element. This approach is similar to printer/scanners where paper is pulled by a powered roller across a scanning element to accomplish the scanning process. In this embodiment the bottle is held against the rollers by the gravity of its own weight. Alternatively, the cradle could be oriented vertically with the inclusion of counter pressure rollers located opposite to the main rollers. The vertical system could include base rollers or turntable elements to eliminate rotational friction forces at the base of the bottle, or to power the rotation motion. Both embodiments are particularly well suited to accommodating different diameter bottles because the label maintains a constant distance from the scanning element.

In still another embodiment, the scanning apparatus may comprise a hand-held scanner. The hand-held scanner would provide flexibility to scan a bottle label at a remote location. Preferably, such a hand-held scanner apparatus would use a roller system to measure and compensate for the different manual scan speeds of the individual users. Such roller systems are well known to those skilled in the art.

In a further embodiment, a charge coupled device (hereinafter "CCD") or device with a lens that compensates for the curvature of the label may be used. With the CCD embodiment, the compensating lens presents an image of the label in a flat plane and that image is transferred through a focusing lens to the CCD device from which the stored image may be transferred to any remote storage device. A frame holds the entire assemblage in the proper relationship such that the user simply places the frame against the curved surface and the image can be captured.

In another embodiment, it is possible to use only a focusing lens and the CCD chip to image the object. This system eliminates the compensating lens. This system compensates for the curvature by optimizing depth of field settings; thus, to obtain a clear image, proper lighting, proper focusing distance, and the quality of the lens all become increasingly important. The system can be properly adjusted and placed in a frame to hold the elements in the proper relationship to each other. Such a system would also be preset and non-adjustable to function properly and require no expertise in using it. The frame need only be placed against the curved surface from which the image is to be taken.

The image obtained may be transferred to a variety of output or storage devices. Such output and storage devices could be anything from basic printing to other electronic media that may include digital disk storage, memory chips, CD's, DVD's, and other commonly used computer peripherals. Similarly, the information may be transferred to other devices such as wireless networks, computers, and hand-held PDA's.

A preferred embodiment of the novel invention allows a simple and convenient scanning of wine labels to generate data that is outputted to various means that can be supplied to wine consumers in real time in a dynamic restaurant environment. In addition, the restaurant merchant may wish to provide the customer with other information as part of the reproduced label such as restaurant information, food eaten, the date on which the event took place, company present, and the like.

A controller, such as a microprocessor, may be associated with the scanning apparatus to activate the scanning function, input additional textual information, and then transfer the electronic image to a printer, a remote device such as a digital disk storage unit, memory chips, CD's, DVD's, PDA's and the like.

Thus, it is an object of the present invention to provide a simple apparatus and method for convenient scanning and imaging of arcuate surfaces and, in particular, wine bottle labels.

It is also an object of the present invention to provide an apparatus comprising an imaging chamber into which to place the bottle whose label is to be scanned and being capable of rotating the bottle with respect to the scanner to obtain an image of the label.

It is still another object of the present invention to scan the arcuate surface or bottle label with an apparatus comprising a scanner that moves in a predetermined track around the bottle in at least an arcuate path.

It is yet another object of the present invention to scan the arcuate surface or bottle label with an apparatus comprising a rotating base such as a rotating turntable or series of rollers that moves the bottle label past a fixed scanning device. Such apparatus may also include a means for compensating for different diameter bottles and for providing a centering means for the axis of rotation, such as a movable arm opposite the scanner.

It is yet another object of the present invention to provide such an apparatus wherein the imaging chamber is configured as a cradle comprising an array of motorized rollers, whereby the bottle is rotated and the label passes across a fixed scanning element.

It is also an object of the present invention to associate a controller, preferably in the form of a microprocessor, with the scanner to activate the scanning function; automatically adjust the received image for features such as quality, position, and size; and transmit the scanned label image to a remote storage and/or processing device.

It is still another object of the present invention to use a hand-held image scanning device to scan a bottle label.

It is also an object of the present invention to provide an apparatus for scanning arcuate surfaces, such as wine bottle labels, comprising a frame that holds a focusing lens and CCD chip in the proper fixed relationship to image the curved surface.

It is another object of the present invention to provide such apparatus that also holds a compensating lens, if desired, in proper relationship with the focusing lens and the CCD chip to properly and clearly image the arcuate surface.

Thus, the present invention relates to a method for imaging a bottle label comprising the steps of placing the bottle in an imaging chamber, and scanning at least the label of a bottle with a scanner that moves in a least an arcuate path with respect to the bottle along a given radius from the center of the chamber to image the label, or, rotating the bottle with respect to a stationary scanner. In a preferred method, ambient light is excluded from the chamber.

The invention also relates to apparatus for imaging a bottle label comprising an imaging chamber for receiving a bottle with a label to be scanned and a scanner associated with the imaging chamber for imaging the bottle label, wherein either the scanner travels in at least an arcuate path with respect to the bottle along a given radius from the center of the bottle, or the bottle is rotated with respect to a stationary scanner. A preferred embodiment comprises a means for excluding ambient light from the chamber.

BRIEF DESCRIPTION OF THE DRAWINGS

These and other more detailed objects of the present invention will be disclosed when taken in conjunction with the following Detailed Description of the Drawings in which like numerals represent like elements and in which.

DETAILED DESCRIPTION OF THE DRAWINGS

Figure 1A:
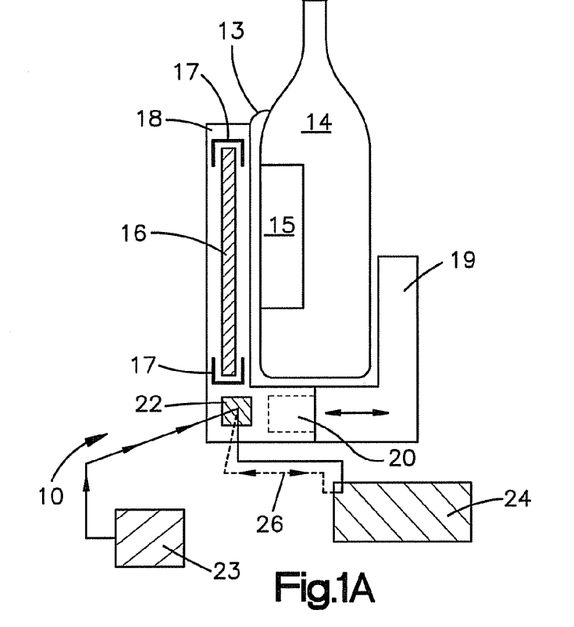
FIG. 1A, is a side cross-sectional view of a first embodiment of an apparatus of the present inventions having a bottle placed within an adjustable imaging chamber in which a scanner moves in an arcuate path.
Figure 1B:
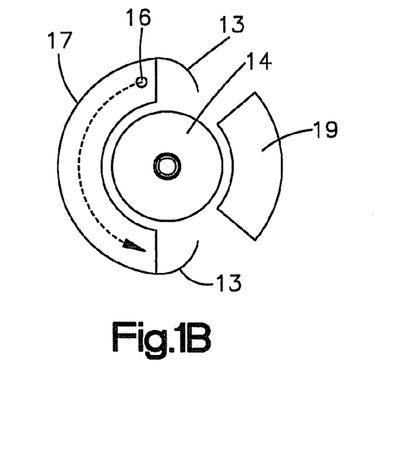
FIG. 1B is a top plan view of the chamber portion of the embodiment of FIG. 1A, illustrating the arcuate movement of the scanning device with respect to a bottle.

FIG. 1 is a schematic representation of a first embodiment of the novel invention. The apparatus 10 comprises an imaging chamber 12. Chamber 12 can be in the form of a unitary, substantially cylindrical body. Alternatively, chamber 12 can comprise two or more partial cylinder walls 18, 19 that can be adjusted away from or toward each other to accommodate different diameter bottles. In the illustrated embodiment, partial cylinder wall 19 has at its base a protuberance 20 that extends into a corresponding slot in the base of particularly cylinder wall 18. A wine bottle 14 with label 15 is placed within the imaging chamber 12. Any well-known type of imaging device 16, such as a scanner, may be associated with a wall of the imaging chamber 12 as shown. In the illustrated embodiment, the scanner or imaging device 16 moves along arcuate guide means 17 in at least an arcuate path about the bottle 14 to scan the label 15. This arcuate movement is analogous to the movement of a scanning device in one plane as in conventional flatbed scanners, but with the scanner guide means 17 defining an arcuate path rather than a linear path. Thus, the novel arcuate path scanner can utilize a conventional scanning mechanism, such as a motor 12, linkage (not shown for clarity), and guide means 17, but with the guide means 17 defining an arcuate or circular path instead of a linear path as in a flatbed scanner. One skilled in the art would know how to make and use such a device. In the present invention, the arcuate path is defined by guides 17 at the top and/or bottom of the imaging chamber 12.

In a preferred embodiment, one ore more flexible skirts or aprons 13 cover the space at the top of the imaging device 16 between the bottle 14 and the inner wall of the imaging chamber 12 to exclude ambient light from entering the imaging chamber 12. Additional light blocking flexible skirts 13 can be disposed at the vertical edges of partial cylinder wall 18.

A controller 22, preferably in the form of a microcomputer, can be programmed to control the movement of the imaging device 16 along the arcuate path formed by the guides 17. It also can be programmed to enable the scanned image to be transmitted along path 26 either to a device 24 such as a printer for printing; alternatively, device 24 can be a storage device, such as a digital disk storage unit, memory chips, CD's, DVD's, PDA's, and the like. As is known in the art, such transmission can be accomplished either wirelessly or along a circuit. As stated above, the controller 22 can cause the scanner 16 to move in a circle about the bottle 14 or in an arcuate path just covering the label 15 to be scanned. Associated with controller 22 is an optional input device such as a keyboard or other data entry device shown schematically as block 23. With the data entry device, any desired textual information could be added to an output format of the scanned label, such as date, restaurant, food ordered, and persons present. In addition, information regarding the label 15 could be entered. Such information could include a copyright notice caveat, a statement of use such as "For label collector's use only", and the like. Of course the microprocessor or controller 22 could be programmed to add any desired appropriate message to an output format that includes the scanned image of label 15.

The controller 22 can be disposed within a wall of the imaging chamber 12, as shown in FIG. 1A. Alternatively, controller 22 could be located apart from the imaging chamber 12, and coupled thereto with appropriate cables or wireless transmitting devices. The controller 22 also may be programmed to automatically adjust the scanned image for correct reproduction.

Figure 2A:
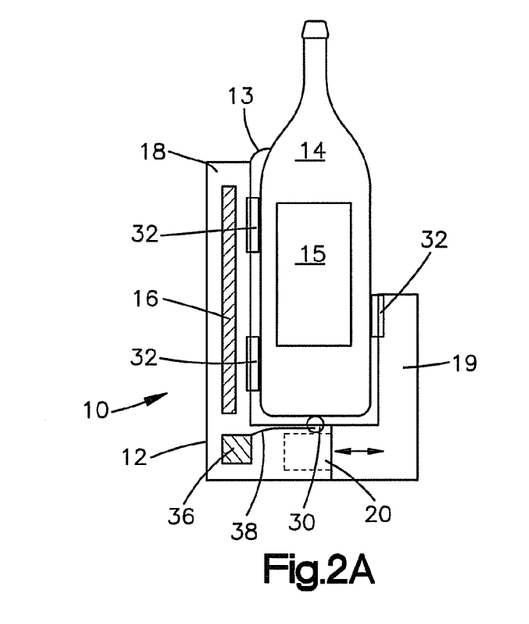
FIG. 2A is a side cross-sectional view of the chamber of a second embodiment of an apparatus of the present invention having an adjustable imaging chamber in which a bottle is rotated past a fixed scanning element.
Figure 2B:
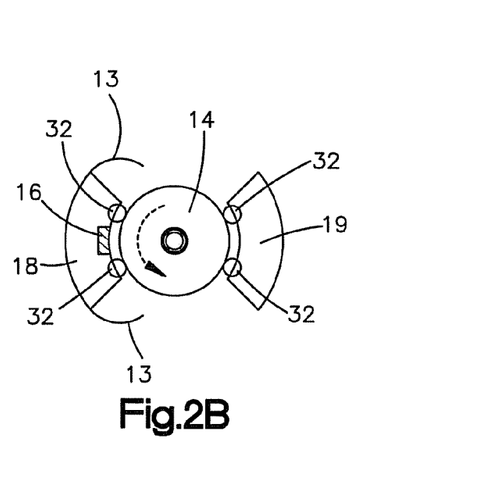
FIG. 2B is a top plan view of the chamber portion of FIG. 2B, showing the rotation of the bottle with respect to a fixed scanning element.

FIGS. 2A, 2B illustrate a second embodiment of the present invention. In this embodiment, instead of moving the imaging device 16 along the arcuate path defined by guides 18, a rotating base 30 may be placed in the bottom of the imaging chamber 12 and rotated in a given direction by motor 36 coupled to rotating base 30 by drive system 38, all under the control of microprocessor 22, omitted for charity. In such case, the imaging device 16 is fixed and the bottle with the label is rotated past the fixed imaging device 16 and imaged. The rotating base 30 can be, for example, either a turntable or a plurality of rollers. In this embodiment, it is important that the bottle be properly centered on rotating base 30. This can be accomplished by proper adjustment of partial chamber wall 19 with respect to partial chamber wall 18. Additionally, rollers 32 disposed on the inner surfaces of chamber walls 18, 19 can serve as means for centering a bottle 14 within chamber 12. Again, such operation would be easily understood by one skilled in the art.

As in the first embodiment, the output device, which may be a printer or other means including electronic or computer media, may be contained within the main apparatus or could be separately connected via wires or wireless means.

FIG. 2B is a top view of the imaging chamber 12 with a bottle 14, shown in cross-section, placed therein. The imaging device or scanning element 16 is shown within the walls of the imaging chamber 12. An arrow indicates the direction of rotation of bottle 14. The optional flexible skirts or aprons 13 are shown covering the spaces between the inner wall of the imaging chamber 12 and the bottle 14 to prevent ambient light from entering therein. The microprocessor 22 and optional input device 23 and output device 24 as shown in FIG. 1 would also be used in FIG. 2 but are omitted for clarity. It will be understood by those skilled in the art that if a fixed scanner or imaging device 16 is used in FIGS. 2A, B, then the rotating base 30 would rotate bottle 14 in the same or the opposite direction under the direction of the controller or microprocessor 22 so that label 15 will pass the fixed scanner 16.

Figure 3A:
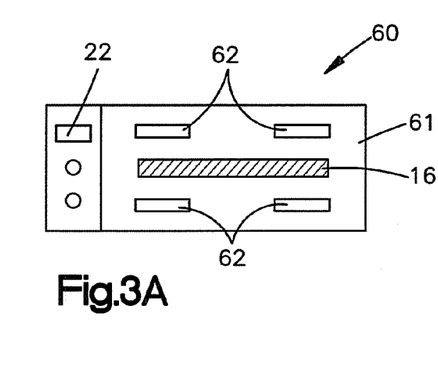
FIGS. 3A, B, C are top plan, side elevation, and front elevation views, respectively, of a third embodiment of an apparatus of the present invention, wherein the imaging chamber is configured as a cradle in the horizontal orientation and having a roller system whereby the bottle label is rotated past a fixed scanning element.
Figure 3B:
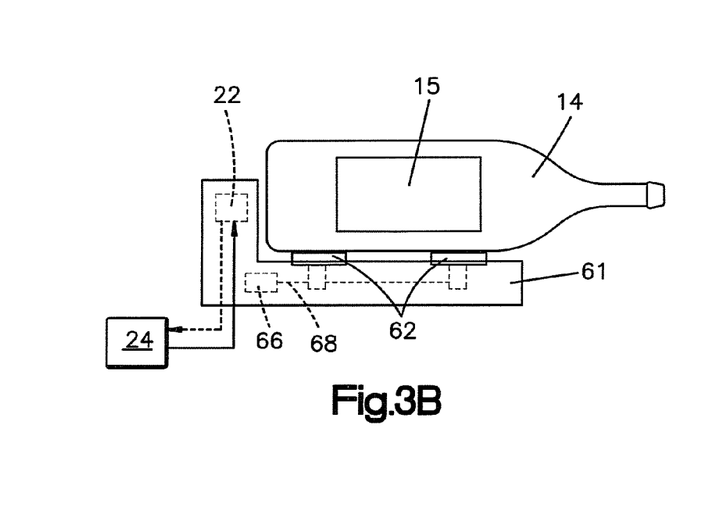
Figure 3C:
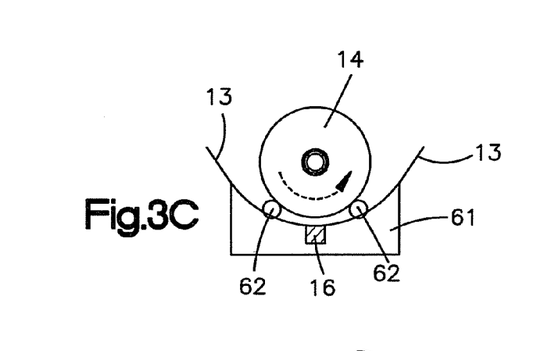

FIGS. 3A, 3B, and 3C illustrates a top plan view, a side elevation view, and a front elevation view, respectively, of yet another embodiment 60 of the present invention. In this embodiment, chamber 12 is configured as a curved cradle 61 disposed in a substantially horizontal orientation. The inner surface of the cradle 61 is provided with a plurality of rollers 62 and a fixed scanning element 16. A bottle 14 is placed horizontally on the rollers. One or more of the rollers 62 is powered by motor 66 and drive system 68, indicated by phantom lines in FIG. 3B. Rotation of the roller 62 causes bottle 14 to rotate such that label 15 passes across fixed scanning element 16. The weight of bottle 14 holds it in proper position against rollers 62. Thus, this embodiment can more easily accommodate bottles of different diameters Light-blocking flexible skirts 13 can be disposed along the edges of cradle 61 to exclude ambient light while the image of label 15 is being scanned. System 60 can be controlled by controller 22, which can be disposed within a housing of cradle 61, as shown in FIGS. 3A, 3B, or can be separate. Output device 24 can be a printer or storage device as described above.

Figure 4:
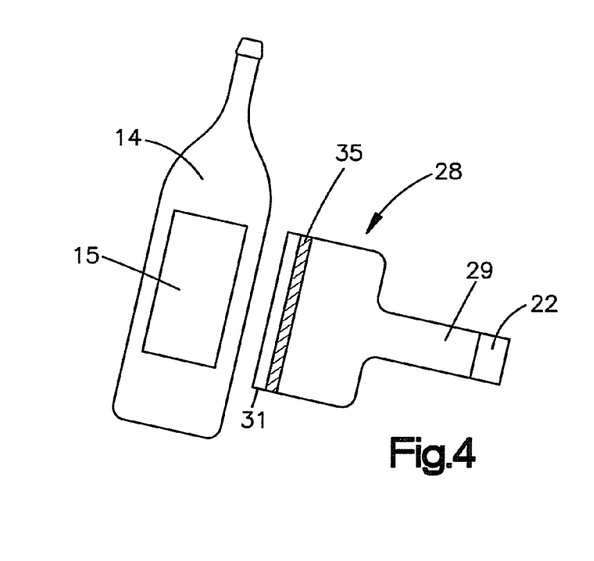
FIG. 4 is a side view of a fourth embodiment of an apparatus of the present invention in which the scanning element is hand-held.

FIG. 4 illustrates yet another embodiment, in which a hand-held scanner is used to scan the bottle label. The hand-held scanner 28 can have a handle 29 in which a controller 22, such as a microprocessor, is located. On the scanning portion 35, a flexible shield 31 preferably is provided to exclude light from the region being scanned while the scanner 28 is being moved over the label 15 on bottle 14. Again, the controller 22 has storage means for storing the scanned data. Such data can be sent to a printer or wirelessly transmitted to a remotely located device as explained above with respect to the controller of FIG. 1.

Figure 5A:
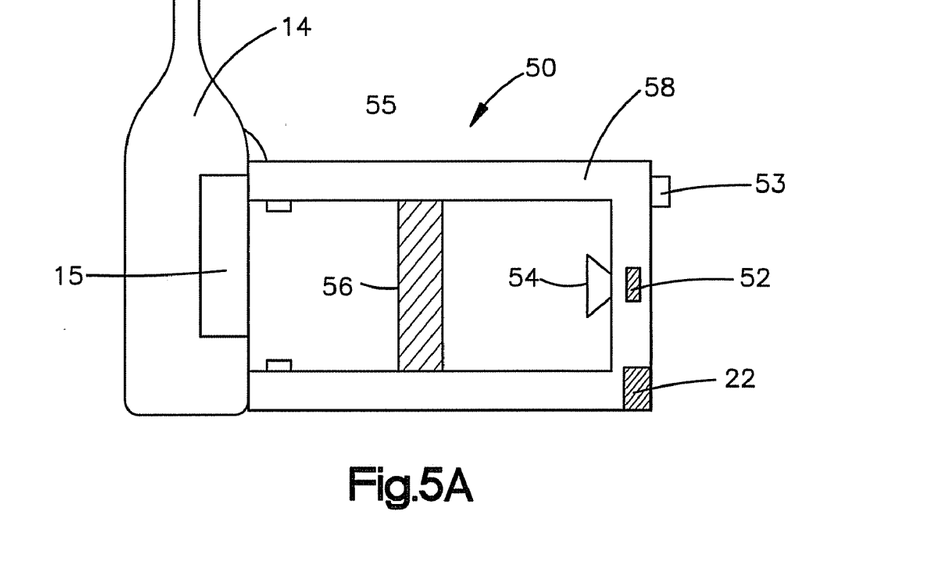
FIG. 5A, is a side view in partial cross-section of a fifth embodiment of an apparatus of the present invention in which a frame holds a compensating lens, a focusing lens, and a CCD chip in proper relationship with each other to form a simple apparatus for imaging an arcuate surface such as a wine bottle.

FIG. 5A is a schematic representation of an imaging system 50 that has no moving parts. The system 50 includes a CCD chip 52, a focusing lens 54 and, optionally, a compensating lens 56 all held in proper relationship with each other with a frame 58. The frame facilitates use of the device in a simple manner by one without expertise with regard to the type of lenses to be used, the proper distance between the focusing lens and the CCD chip 52 and, if used, the proper distance of the compensating lens 56 from the label 15 or other arcuate surface.

The compensating lens 56 can be used to correct for the different depths of field on the label 15 or other arcuate surface that is to be imaged. It provides a focused image 57 on its reverse side as shown in FIG. 5B.

As shown in FIG. 5A, lights 55 can be provided on the frame 58 to provide proper illumination of the image to be captured. Also, for those who are unskilled in the art, microswitches 53 can be provided on the outer end of the frame 58 to actuate when the frame 58 is properly positioned with respect to the arcuate surface to be imaged. These can be used to provide power to an indicator of any desired type such as, for example only, the lights 55 to indicate to the user that the frame is properly positioned against the arcuate surface. The system can be controlled by controller 22 mounted to frame 58.

Figure 5B:
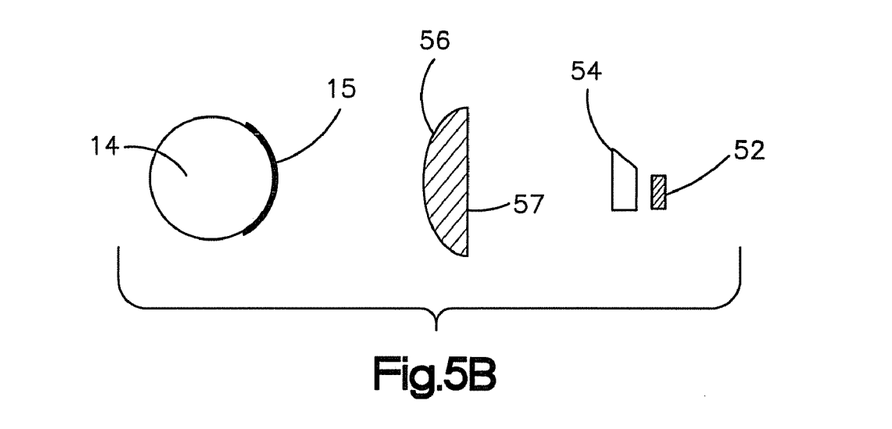
FIG. 5B is a top plan view of the embodiment of FIG. 5A in which the frame is omitted for the sake of clarity.

As stated previously, FIG. 5B is a side view of the system shown in FIG. 5A with the frame 58 being omitted for purposes of clarity of the drawings. It will be seen that the compensating lens 56, if used, causes an image of the arcuate surface, or label 15, to be present on its rear surface as a plane view 57 thus resolving the different depth of fields that occur with relation to the label or arcuate surface.

As stated earlier, if desired, the compensating lens 56 can be eliminated with the use of frame 58 to hold the proper focusing lens 54 at a proper fixed distance between the arcuate surface 15 and the focusing lens 54 to be imaged to correct for different depths of field on the arcuate surface or label 15 and the proper fixed distance between the focusing lens 54 and the CCD chip 52. Such fixed system will allow a novice to use the device, or system 50, with a minimum of instruction.

Figure 6:
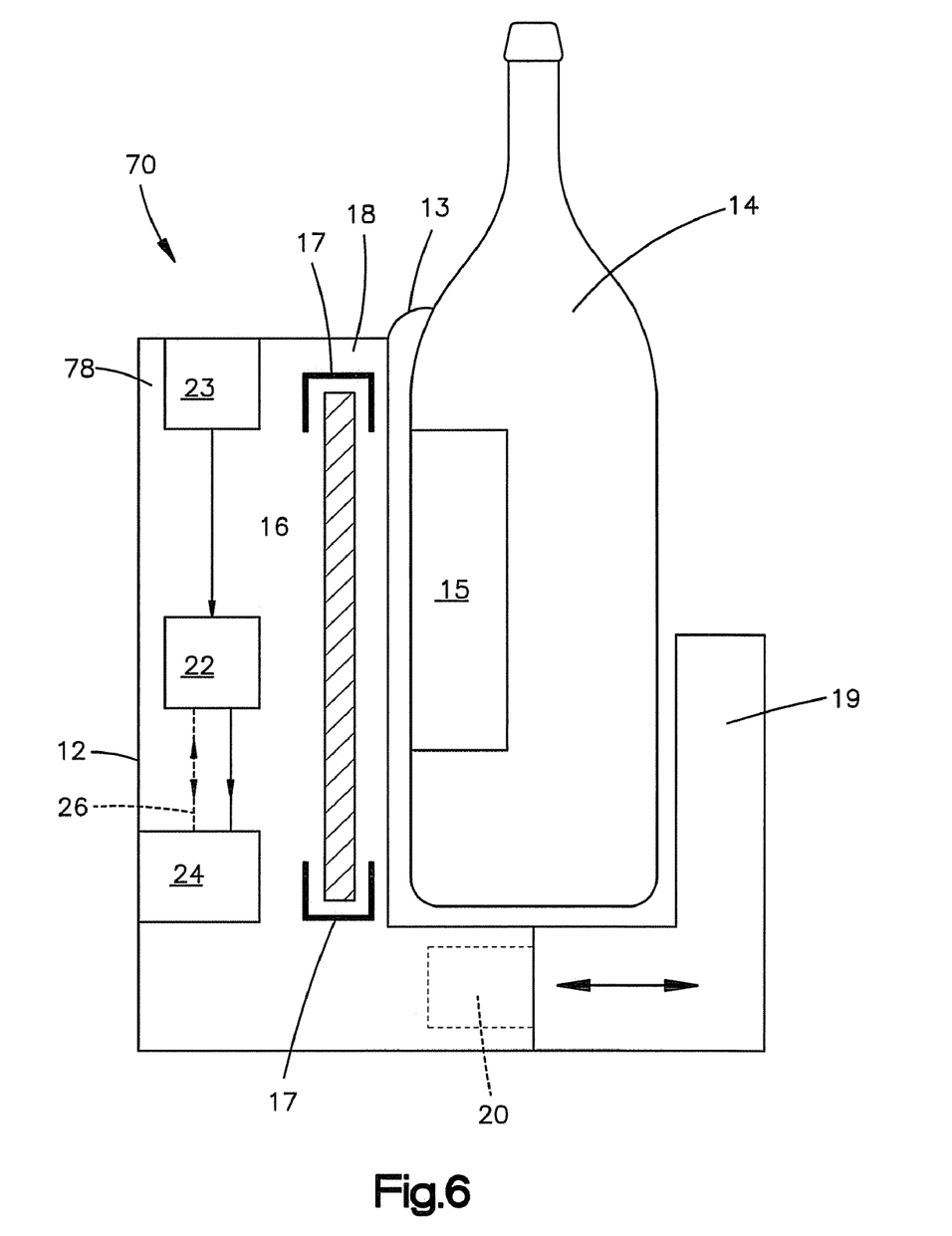
FIG. 6 illustrates an embodiment similar to that of FIG. 1A but wherein all components of the apparatus are disposed within a housing to provide an all-in-one system.

Further, in any of the embodiments disclosed herein, an output device 24, whether it be a printer or another device disclosed herein, can be either a separate element or an integral unit, such as integral with the housing for image chamber 12, or for hand-held scanner 28, or frame 58. Thus an apparatus in accordance with the present invention can comprise separate components, or can be an all-in-one system, as may be desired for any particular application. For example, FIG. 6 illustrates an embodiment of the invention very similar to that shown in FIG. 1A, except that the housing 78 of partial cylinder wall 18 is enlarged so as to accommodate therein not only controller 22 but also input device 23, output device 24, and the circuitry therebetween, including path 26. It will be appreciated that any of the embodiment of FIGS. 2-5 could also be so modified to present such an all-in-one system.

Thus, there has been disclosed a novel bottle label scanning means that allows a label to be scanned, and the resulting image to be downloaded, and printed or otherwise transmitted to a remote device. The imaging chamber allows the scanner to be moved in an arcuate direction about the bottle to scan the label or, alternatively, allows the scanner to be stationary while the bottle and label are rotated on a turntable or rollers in front of the imaging device.

In still another embodiment, there are no moving parts and the arcuate surface, or label, to be imaged is focused by a lens on the recording medium such as a CCD chip.

While particular embodiments of the invention have been shown and described in detail, it will be obvious to those skilled in the art that changes and modifications of the present invention, in its various embodiments, may be made without departing from the spirit and scope of the invention. Thus, while the apparatus and method of the present invention have been described in terms of obtaining an image of a label on a wine bottle, it will be recognized that the invention is not so limited, and may be used to obtain an image of any feature on any arcuate surface. Other elements, steps, methods, and techniques that are insubstantially different from those described herein are also within the scope of the invention. Thus, the scope of the invention should not be limited by the particular embodiments described herein but should be defined by the appended claims and equivalents thereof.

The invention claimed is:

1. A method of capturing an image of a wine bottle label on an exterior of a bottle of a wine, the label comprising artwork, the method comprising the steps of:
   placing the wine bottle in an imaging chamber of a portable imaging device operable to hold only a single bottle of wine at a single time;
   creating relative arcuate motion between the portable imaging device and the bottle of wine through actuation of the portable imaging device through a controller of the imaging device;
   and capturing an image of the wine bottle label during the relative arcuate motion;
   wherein the controller is operable to add textual data not present on the wine bottle label to an output format of the captured image, print an output format of the image both with or without added textual data, electronically save the image both with or without added textual data, and automatically adjust the image quality both with or without added textual data.

2. The method of claim 1 wherein said imaging device is moved while the wine bottle is stationary.

3. The method of claim 1 wherein the bottle of wine is moved while the imaging device is stationary, the image being obtained while said bottle of wine is in motion.

4. The method of claim 1 wherein said imaging device is a scanner.

5. The method of claim 1 wherein said imaging device is moved with respect to the wine bottle in said chamber, and said imaging chamber comprises guide means that define an arcuate path along which said imaging device moves with respect to the wine bottle.

6. The method of claim 1 wherein the bottle of wine is moved with respect to said imaging device, and said imaging chamber comprises means for moving the bottle of wine with respect to said imaging device.

7. The method of claim 1 comprising the further step of excluding at least some ambient light from said imaging chamber.

8. The method of claim 1 wherein said controller is a microprocessor.

9. The method of claim 8 comprising the further step of programming the microprocessor to automatically adjust the optimum depth of field of the image for one or more of quality, position, and sizing.

10. The method of claim 8 comprising the further step of transmitting the retained image to a device selected from the group consisting of a printer and a remote storage device.

11. The method of claim 10 wherein said transmission is accomplished wirelessly.

12. The method of claim 10 comprising the further step of providing input data to the microprocessor, said input data to be added to an output format of the image.

13. The apparatus of claim 1 wherein said means for capturing an image of the wine bottle label comprises a scanner.

14. Apparatus as in claim 13 wherein said controller is associated with the scanner for activating the scanning function.

15. Apparatus as in claim 14 wherein said controller is a part of an integral unit with said imaging chamber.

16. Apparatus as in claim 14 wherein said controller is remote from said imaging chamber.

17. Apparatus as in claim 14 wherein said controller comprises a microprocessor.

18. Apparatus as in claim 17 further comprising:
a remotely located image storage device; and
a wireless transmitter associated with the microprocessor for wirelessly transmitting the scanned image to said remote storage device.

19. Apparatus as in claim 17 further comprising an image storing device and a means for transmitting the scanned image to said storage device, said storage device and transmitting means being disposed within an integral unit with said imaging chamber.

20. Apparatus as in claim 17 further comprising data input means coupled to the controller for adding textual information to an output format comprising the scanned image.

21. Apparatus as in claim 20 wherein said data input means coupled to said controller is disposed within an integral unit with said imaging chamber.

22. Apparatus as in claim 14 wherein said scanner is stationary relative to said imaging chamber, said means for creating relative arcuate motion between the portable imaging device and the bottle of wine comprising:
a rotating means positioned within the imaging chamber for rotational movement of the wine bottle; and
said controller being coupled to said rotating means for controlling the rotation of the rotating means to cause the wine bottle label to be imaged by the stationary scanner.

23. Apparatus as in claim 22 wherein said rotating means is selected from the group consisting of a turntable and rollers.

24. A portable apparatus for capturing an image of a wine bottle label on an exterior of a bottle of wine, the label comprising artwork, the apparatus comprising:
an imaging chamber operable to hold only a single bottle of wine at a single time;
means for creating relative arcuate motion between the portable imaging device and the bottle of wine through actuation of the portable imaging device through a controller of the imaging device;
and means for capturing an image of the wine bottle label during the relative arcuate motion;
wherein the controller is operable to add textual data not present on the wine bottle label to an output format of the captured image, print an output format of the image both with or without added textual data, electronically save the image both with or without added textual data, and automatically adjust the image quality both with or without added textual data.

25. The apparatus of claim 24 wherein said imaging chamber is selected from the group consisting of a substantially unitary vertical cylinder; a substantially vertical chamber comprising two or more partial cylinder walls; and a horizontal cradle.

26. Apparatus as in claim 25 wherein said chamber is a substantially unitary vertical cylinder or a substantially vertical chamber comprising two or more partial cylinder walls, said apparatus further comprising:
one or more guide means for receiving the scanner and defining an arcuate path to cause the scanner to move in the arcuate path about the wine bottle within the guide means.

27. Apparatus as in claim 26 wherein said one or more guide means causes the scanner to move in a circular path about the wine bottle.

28. The apparatus of claim 24, said means for capturing an image of the wine bottle label during the relative arcuate motion comprising: a first device for providing a focused image of the wine bottle label, the focused image being compensated for depth of field differences; a second device for receiving and recording the focused image of the wine bottle label, the focused image comprising the artwork that appears on the wine bottle label.

29. The apparatus of claim 28
wherein said controller is associated with the second device for activating the second device to receive and record the focused image of the wine bottle label; and
further comprising data input means associated with the controller for adding textual data to an output format comprising the recorded focused image.

30. The apparatus of claim 29 further comprising transmission means associated with the controller for transmitting the focused image and any added textual data to a remotely located device for storage and/or use.

* * * * *